United States Patent
Crawford

(10) Patent No.: US 7,144,388 B2
(45) Date of Patent: Dec. 5, 2006

(54) SELECTIVELY PASSIVE SHIELDABLE MEDICAL NEEDLE DEVICE

(75) Inventor: Jamieson Crawford, New York, NY (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 70 days.

(21) Appl. No.: 10/725,089

(22) Filed: Dec. 1, 2003

(65) Prior Publication Data

US 2005/0119635 A1 Jun. 2, 2005

(51) Int. Cl.
A61M 5/32 (2006.01)

(52) U.S. Cl. .............. 604/192; 604/263; 604/177; 604/506; 604/110

(58) Field of Classification Search ............ 604/110, 604/164.08, 165.03, 177, 187, 192, 197, 604/198, 263, 268, 500, 506; 128/919
See application file for complete search history.

(56) References Cited

U.S. PATENT DOCUMENTS

| | | | |
|---|---|---|---|
| 3,064,648 A * | 11/1962 | Bujan ................ 604/177 |
| 4,886,503 A | 12/1989 | Miller |
| 4,944,397 A | 7/1990 | Miller |
| 4,976,699 A | 12/1990 | Gold |
| 4,982,842 A | 1/1991 | Hollister |
| 5,017,189 A | 5/1991 | Boumendil |
| 5,055,102 A | 10/1991 | Sitnik |
| 5,078,693 A | 1/1992 | Shine |
| 5,098,382 A | 3/1992 | Haber et al. |
| 5,139,489 A | 8/1992 | Hollister |
| 5,151,089 A * | 9/1992 | Kirk et al. ............ 604/192 |
| 5,154,285 A | 10/1992 | Hollister |
| 5,188,611 A | 2/1993 | Orgain |
| 5,192,275 A * | 3/1993 | Burns ................ 604/263 |
| 5,232,454 A | 8/1993 | Hollister |
| 5,232,455 A | 8/1993 | Hollister |
| 5,242,417 A | 9/1993 | Paudler |
| 5,277,311 A | 1/1994 | Hollister |
| 5,312,366 A | 5/1994 | Vailancourt |
| 5,312,368 A | 5/1994 | Haynes |
| 5,312,369 A * | 5/1994 | Arcusin et al. ........... 604/192 |
| 5,348,544 A * | 9/1994 | Sweeney et al. ........... 604/192 |
| 5,374,255 A * | 12/1994 | Nathan et al. ........... 604/192 |
| 5,401,251 A | 3/1995 | Hui |
| 5,490,841 A | 2/1996 | Landis |
| 5,509,907 A | 4/1996 | Bevliacqua |
| 5,584,816 A | 12/1996 | Gyure et al. |
| 5,584,818 A * | 12/1996 | Morrison ................ 604/197 |
| 5,599,313 A * | 2/1997 | Gyure et al. ............ 604/192 |

(Continued)

Primary Examiner—Nicholas Lucchesi
Assistant Examiner—Theodore J. Stigell
(74) Attorney, Agent, or Firm—Mark J. Schildkraut; Mark Lindsey

(57) ABSTRACT

A pivotable shielding needle device for shielding used needle cannulas. The device generally includes a hub with a needle, and a shield pivotable between a first position exposing the needle and a second position encompassing the needle. A biasing element acts on the shield to pivotally bias it toward the second position, with the shield maintained in the first position through a latch mechanism extending between the shield and the hub. A release arrangement extends from the hub and is squeezable to cause movement of a movable member which releases the latch mechanism, thereby causing the shield to be pivotally biased to the shielding position. Accordingly, activation and shielding of the needle can be effectively accomplished during removal of the needle device from a patient, thereby providing for passive activation of the device during normal use.

15 Claims, 8 Drawing Sheets

U.S. PATENT DOCUMENTS

| | | | |
|---|---|---|---|
| 5,599,318 A * | 2/1997 | Sweeney et al. ............ 604/263 |
| 5,603,699 A | 2/1997 | Shine |
| 5,662,617 A | 9/1997 | Odell et al. |
| 5,669,889 A | 9/1997 | Gyure et al. |
| 5,672,160 A * | 9/1997 | Osterlind et al. ........... 604/263 |
| 5,672,161 A * | 9/1997 | Allen et al. ................. 604/263 |
| 5,681,295 A * | 10/1997 | Gyure et al. ................ 604/263 |
| 5,693,022 A * | 12/1997 | Haynes ....................... 604/192 |
| 5,733,265 A * | 3/1998 | Bachman et al. ........... 604/263 |
| 5,746,726 A * | 5/1998 | Sweeney et al. ............ 604/263 |
| 5,807,351 A | 9/1998 | Kashmer |
| 5,868,716 A | 2/1999 | Sweeney et al. |
| 5,885,249 A | 3/1999 | Irisawa |
| 5,910,130 A * | 6/1999 | Caizza et al. ............... 604/110 |
| 5,913,846 A * | 6/1999 | Szabo ........................ 604/263 |
| 5,993,426 A | 11/1999 | Hollister |
| 6,120,482 A | 9/2000 | Szabo |
| D437,935 S | 2/2001 | Geist |
| RE37,110 E | 3/2001 | Hollister |
| RE37,252 E | 7/2001 | Hollister |
| 6,254,577 B1 | 7/2001 | Huet |
| 6,280,420 B1 * | 8/2001 | Ferguson et al. ........... 604/198 |
| 6,298,541 B1 | 10/2001 | Newby et al. |
| 6,309,376 B1 * | 10/2001 | Alesi .......................... 604/263 |
| 6,319,232 B1 * | 11/2001 | Kashmer .................... 604/192 |
| 6,443,929 B1 * | 9/2002 | Kuracina et al. ........... 604/192 |
| 6,635,032 B1 * | 10/2003 | Ward, Jr. .................... 604/192 |
| 6,796,968 B1 * | 9/2004 | Ferguson et al. ........... 604/198 |
| 6,837,877 B1 * | 1/2005 | Zurcher ...................... 604/263 |
| 6,860,871 B1 * | 3/2005 | Kuracina et al. ........... 604/192 |
| 2003/0181868 A1 | 9/2003 | Swenson |
| 2003/0181874 A1 * | 9/2003 | Bressler et al. ............. 604/263 |

\* cited by examiner

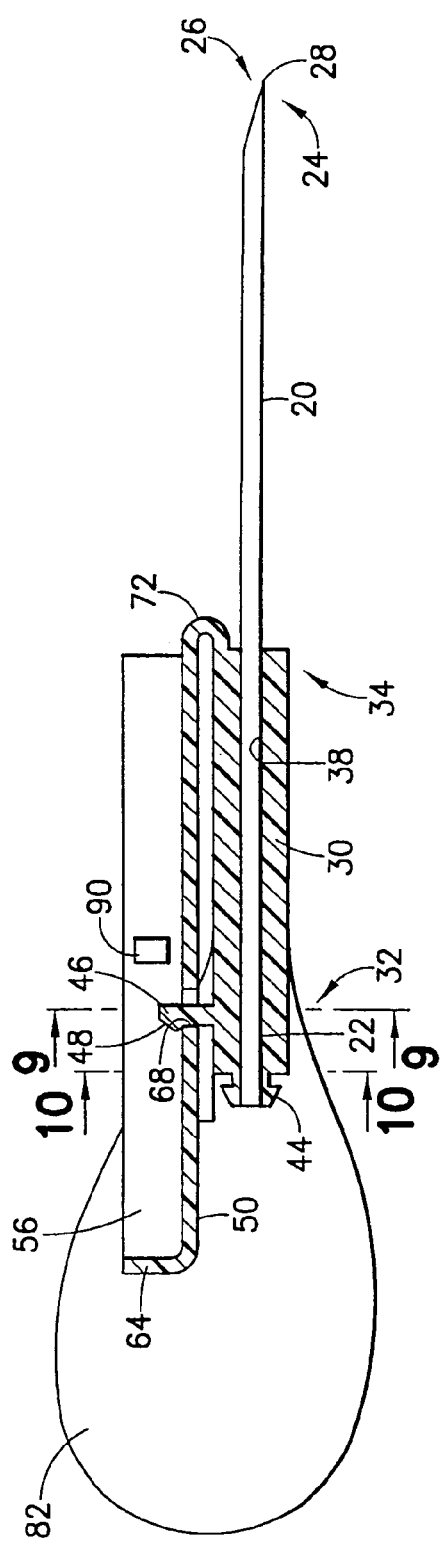
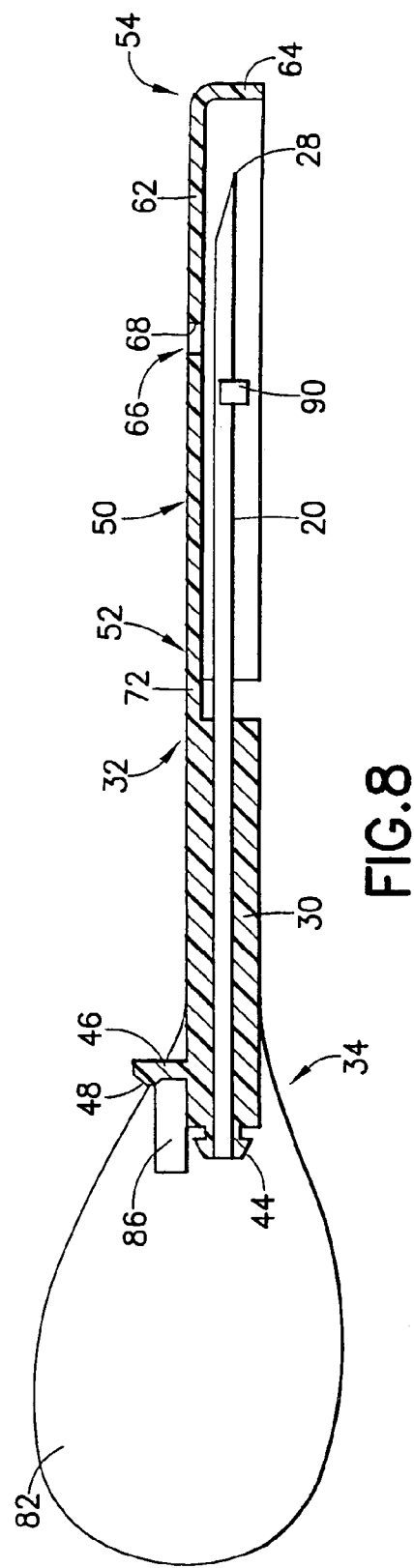
FIG.7
FIG.8

SELECTIVELY PASSIVE SHIELDABLE MEDICAL NEEDLE DEVICE

BACKGROUND OF THE INVENTION

1. Field of the Invention

The present invention relates to a medical device for safe and convenient handling of used needle cannulas. More particularly, the present invention relates to a medical needle device that is adapted to automatically shield a needle cannula during normal use in a medical procedure.

2. Description of Related Art

Blood collection sets or intravenous (IV) infusion sets typically include a needle cannula having a proximal end, a distal end with a puncture tip, and a lumen extending therebetween. The proximal end of the needle cannula is mounted to a plastic hub having a central passage that communicates with the lumen in the needle cannula. A thin flexible thermoplastic tube is connected to the hub and communicates with the lumen in the needle cannula. The end of the plastic tube remote from the needle cannula may include a fixture for connecting the needle cannula to a separate medical device, such as a holder, a blood collection tube, and the like.

In order to reduce the risk of incurring an accidental needle-stick wound, protection of used needle cannulas becomes important. With concern about infection and transmission of diseases, methods and devices to cover used needle cannulas have become important and in great demand. Some needle assemblies commonly employ a safety shield that may be moved into shielding engagement with a used needle cannula without risking an accidental needle stick.

For example, a number of devices incorporate a pivoting shield assembly in which the shield can be pivoted away from the needle during use and pivoted about the needle after use, for protection from the used needle. Such pivotable shielding devices are well known for use in syringe devices, such as those disclosed in U.S. Pat. Nos. 5,599,318; 5,662,617; 5,669,889; 5,681,295; 5,733,265; 5,868,716; and 5,913,846, for example.

U.S. Pat. No. 6,309,376 discloses a winged intravenous infusion assembly which has a needle extending from a base member, with a pivotable housing attached to the base member for enveloping the needle after use. Pivoting of the pivotable housing to envelop and safely shield the used needle cannula, however, requires a two-handed operation by the user, and cannot be effectively accomplished until the device is completely removed from the patient due to the orientation of the pivotable housing with respect to the wings.

U.S. Pat. No. 6,254,577 discloses a hypodermic needle protector which is useful, for example, as an epicardial needle, and which constitutes a single piece of molded synthetic resin including a distal portion which forms a cap in which the distal end of the needle can be housed, and a proximal portion forming a base. The two portions are hinged together through a fold line, and the cap can be manually tilted by movement of the base to tilt or pivot the cap to a position protectively shielding the needle. Since pivoting of the cap portion is based on a fold and is achieved through corresponding manual movement of the base with respect to the fold, the structure is prone to wear due to wearing of the fold.

In view of the foregoing, there is a continuing need for a shielding medical needle device adapted to shield a used needle cannula once a medical procedure is completed.

SUMMARY OF THE INVENTION

The present invention relates generally to a safety needle system in the form of a shielding medical needle assembly for shielding used needle cannulas. The shielding medical needle assembly generally includes a hub housing extending between a proximal end and a distal end, with a needle cannula extending from the distal end of the hub housing toward a distal end portion which preferably includes a puncture tip. The assembly further includes an elongated shield which is pivotably movable between a first position in which the needle cannula is exposed, and a second position which encompasses the needle cannula for protective shielding thereof. A biasing element, such as a leaf spring, acts between the shield and the hub housing to bias the shield toward the second position, and the shield is maintained in the first position against the bias through a latch mechanism extending between the shield and the hub housing. A release arrangement extends from the hub housing and includes a movable portion, such that movement thereof causes engagement with the latch mechanism to release the latch mechanism, thereby causing the biasing element to bias the shield toward the second position. The design and location of the release arrangement facilitates activation of the release arrangement and effective shielding of the needle during removal of the needle device from a patient, thereby providing for a passive activation of the device during normal use.

Desirably, the movable portion of the release arrangement includes a finger tab having a camming surface which is adapted for engagement and release of the latch mechanism upon movement thereof, thereby causing the biasing element to bias the shield toward the second position. The latch mechanism may be in the form of an elongate member including a tab extending from the hub housing and in frictional engagement within a recess or opening in the shield. As such, movement of the finger tab causes the camming surface to cam the tab out of frictional engagement with the recess or opening in the shield. Desirably, the release arrangement includes a pair of finger tabs which are squeezable together, with at least one of the finger tabs including the camming surface as a movable portion.

A locking mechanism such as a cannula lock extending from within the shield may also be provided for maintaining the shield in the second position shielding the needle. Also, a pair of flexible wings may extend from opposing lateral sides of the hub housing for bending to a dorsal position for guided insertion of the assembly into a patient.

In a further embodiment, the present invention is directed to a safety needle assembly which includes a housing having a needle cannula extending from a distal end thereof, and an elongated shield pivotably connected to the distal end thereof. The shield is biased toward a shielding position encompassing the needle cannula, but latched to the housing against the bias. The housing further includes a squeezable release mechanism extending in a proximal direction of the assembly, such as a pair of finger tabs squeezable toward each other. Squeezing of the release mechanism or finger tabs causes release of the shield from the latched position adjacent the housing, thereby permitting the bias to pivot the shield to the shielding position encompassing the needle cannula.

In yet a further embodiment, the present invention is directed to a method for passively activating a safety needle assembly. The method involves providing a safety needle system including a hub housing having a needle cannula extending from a distal end thereof toward a distal puncture tip, a pivotable shield adjacent the hub housing, a biasing element for pivotably biasing the shield toward a shielding position encompassing the distal puncture tip of the needle cannula, and a latch mechanism between the hub housing and the shield for maintaining the shield in a biased state adjacent the hub housing. The safety needle system is inserted into a patient. Grasping of a release mechanism causes release of the latch mechanism to release the shield from the biased state, thereby causing the shield to pivot toward the shielding position. Desirably, the grasping step involves squeezing the release mechanism to cause release of the latch mechanism, which may occur upon withdrawing the safety needle system from the patient.

The hub housing may further include a pair of flexible wings extending from opposing lateral sides thereof. In such an arrangement, the inserting step may involve bending the flexible wings to a dorsal position for guiding the needle cannula into the patient. Preferably, such bending of the flexible wings to a dorsal position does not cause release of the latch mechanism to release the shield from the biased state.

Further details and advantages of the present invention will become apparent from the following detailed description when read in conjunction with the drawings, wherein like parts are designated with like reference numerals and lower case letters are included where necessary to identify specific embodiments of the invention.

DESCRIPTION OF THE DRAWINGS

FIG. 7 is a side cross-sectional view of the needle shield in use with a needle in a retracted position;

FIG. 8 is a side cross-sectional view of the needle shield in use with a needle in a fully pivoted shielding position;

DETAILED DESCRIPTION

FIGS. 1–10 generally illustrate a medical device according to the present invention. The medical device of the present invention generally includes a shieldable safety needle system adapted to enclose or surround a used needle cannula at the end of a medical procedure, such as a blood collection procedure. The medical device may be used as part of a fluid collection set used to collect blood or other fluids from the body of a human or animal. While described herein in terms of a blood collection set 10, it is noted that the medical device of the present invention including the safety needle system may be used with any medical device incorporating a needle, such as a syringe system, a double-ended phlebotomy needle, or the like. Preferably, the medical device includes a portion that is automatically pivotally biased to a safety, needle-enclosing position during normal use by a user of the medical device resulting in a passive activation of the safety features of the assembly, as discussed in detail hereinafter.

Figure 1:
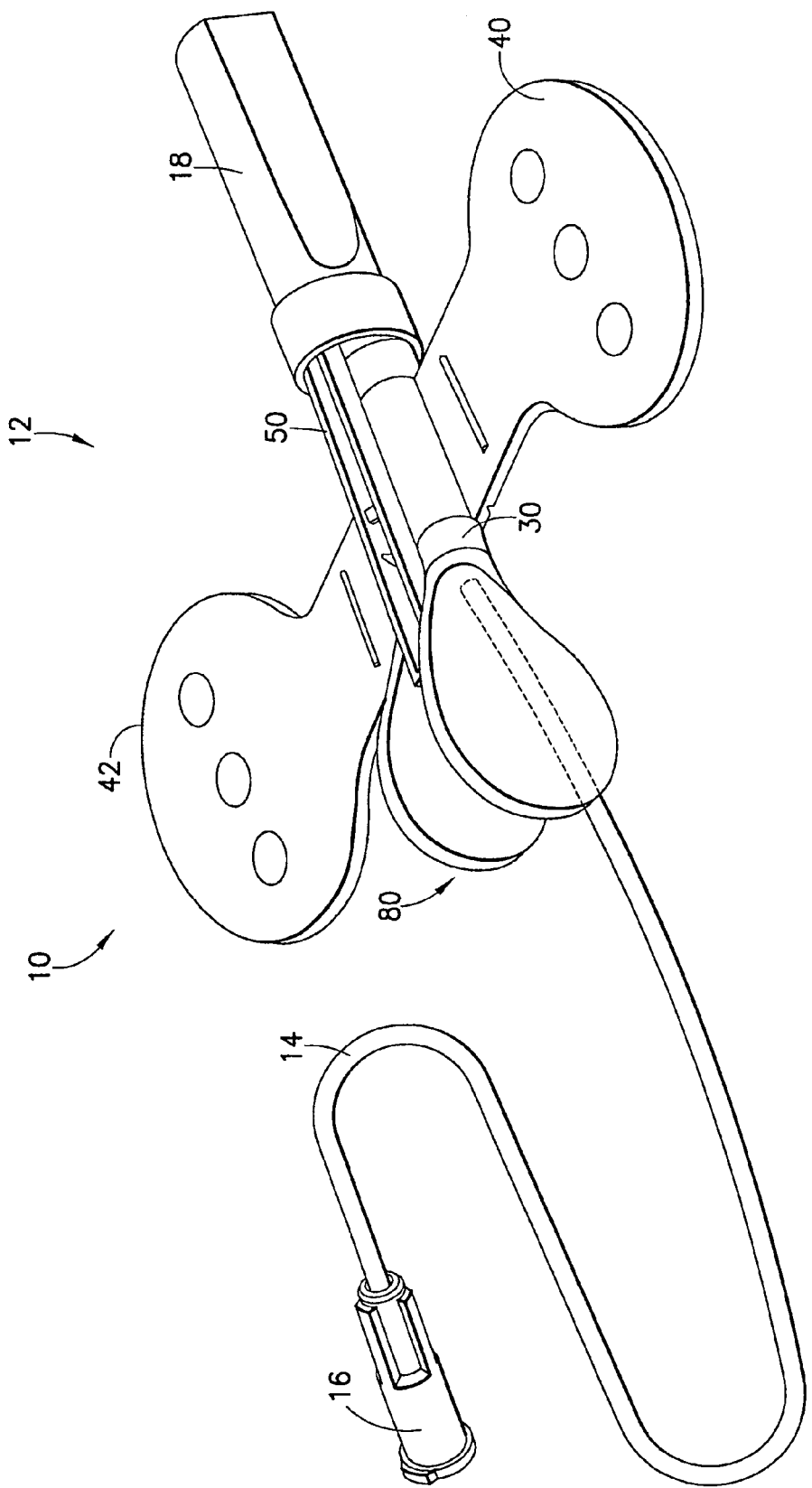
FIG. 1 is a perspective view of the safety needle assembly of the present invention in the form of a blood collection set, shown with a packaging cover maintaining the pivotable needle shield in a retracted position and covering the needle.

Referring to FIG. 1, a first embodiment of the medical device is shown in the form of blood collection set 10. Blood collection set 10 generally includes a shieldable needle device 12, a flexible tube 14 extending from needle device 12, a fixture 16 mounted to tube 14, and a packaging cover 18 removably mounted to portions of needle device 12 opposite tube 14, such as through a frictional engagement. Shieldable needle device 12 of blood collection set 10 is shown in detail in FIGS. 2–10, and generally includes a needle cannula 20, a hub 30, a pivotable shield 50, and a biasing element 70 biasing the shield pivotally away from the hub. A latch mechanism, such as tab 48 extending through opening 66, is provided for maintaining the shield 50 in a biased state adjacent hub 30, and a release arrangement 80 is provided for releasing the latch mechanism. The hub 30 is adapted for connection to a receptacle (not shown) of, for example, a blood collection set, by way of fixture 16 extending from hub 30 through flexible tube 14 by means and procedures known in the art.

As shown in FIG. 7, needle cannula 20 includes a proximal end 22 and an opposing distal end 24, with lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture. Packaging cover 18 is positioned over the distal end 24 of the needle cannula 20 as a removable protective cover to prevent accidental needle-stick wounds prior to using the blood collection set 10 in a medical procedure and to protect the puncture tip 28 prior to use.

Needle assembly 12 further includes housing in the form of hub 30. Hub 30 is a unitary structure, desirably molded from a thermoplastic material. Hub 30 includes a first or proximal end 32, a second or distal end 34, and is defined by a rigid tubular wall extending from proximal end 32 to distal end 34. An internal passage 38 extends through hub 30 from proximal end 32 to distal end 34. Hub 30 may further include a nub 44 extending from proximal end 32 thereof, which provides structure for connection of flexible tube 14 thereto. Alternatively, hub 30 may incorporate structure for attachment to or engagement with an alternate medical device. For example, hub 30 may include a luer fitting, such as a female tapering surface at the proximal end thereof for engagement with a male tapering surface of a separate medical device, such as a syringe barrel.

Figure 2:
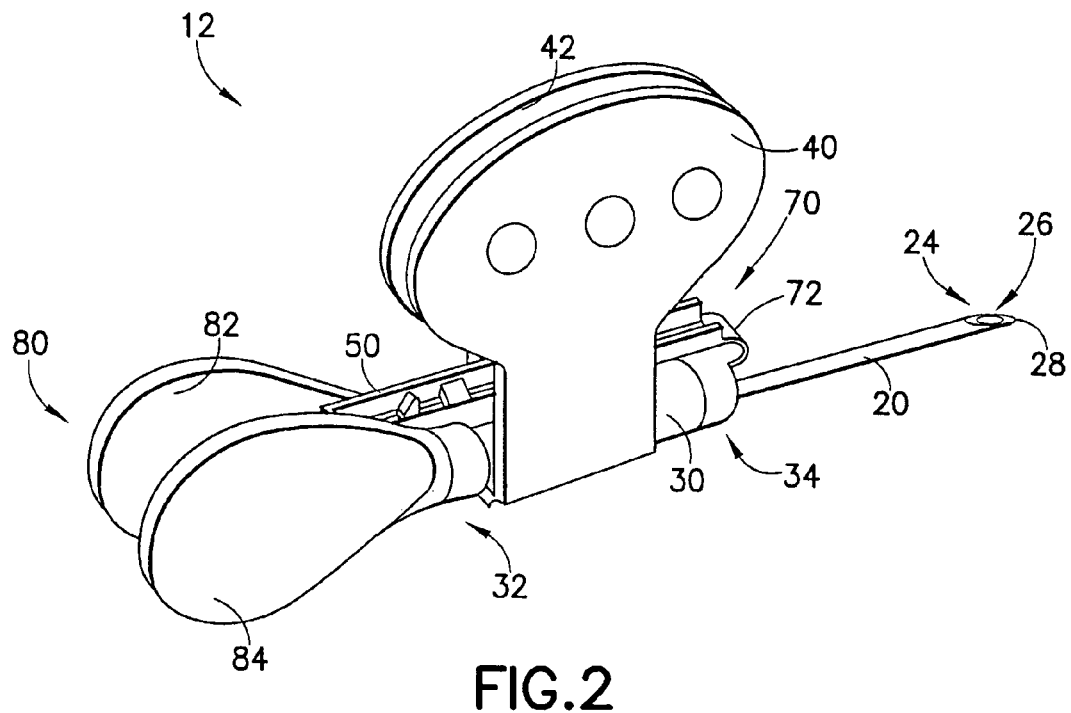
FIG. 2 is a perspective view of the needle device portion of the assembly of FIG. 1 shown with the laterally extending wing members bent into a dorsal position for use during insertion of the needle assembly.

Hub 30 further includes a pair of stabilizers in the form of flexible wings 40 and 42 extending laterally from opposing sides thereof. Wings 40 and 42 provide hub 30, and needle assembly 12, as a butterfly-type wing assembly, for assistance in positioning and placement of needle assembly 12 during a blood collection procedure, and provide a surface for securing needle device 12 to the skin of a patient, such as through taping wings 40 and 42 to the patient's skin. Wings 40 and 42 may be constructed of a flexible material such that at least one, and preferably both, of the wings 40, 42 may be bent toward each other and brought together between the fingers of the user in a dorsal position to assist in positioning and placing the needle device 12 during venipuncture, as shown in FIG. 2.

Needle cannula 20 is positioned within internal passage 38 of hub 30, and extends from distal end 34 of hub 30. Desirably, needle cannula 20 and hub 30 are separate parts which are fixedly attached and secured through an appropriate medical grade adhesive or the like. More particularly, the proximal end 22 of needle cannula 20 is received within the internal passage 38 of hub 30, with the distal end 24 of needle cannula 20 projecting outward from the distal end 34 of the hub 30. The internal passage 38 communicates with the lumen 26 defined in the needle cannula 20 to enable fluid, such as blood, to pass through the needle device 12 and to the flexible tube 14 connecting the needle device 12 to the blood collection receptacle. The needle cannula 20 is preferably secured adjacent the proximal end 32 of hub housing 30 through the use of an appropriate medical grade adhesive, mechanical means, or the like.

Needle device 12 further includes a shield 50 pivotably connected to distal end 34 of hub 30. Shield 50 comprises a first, proximal end 52 and a second, distal end 54. Distal end 54 of shield 50 includes a slot or longitudinal opening 56 formed by sidewalls 58 and 60 that extend downwardly from top section 62 and run substantially opposite of one another in parallel along the length of slot 56 towards forward endwall 64. Shield 50 further includes an opening 66 defining a perimetrical edge 68 extending through top section 62 of shield 50.

Figure 3:
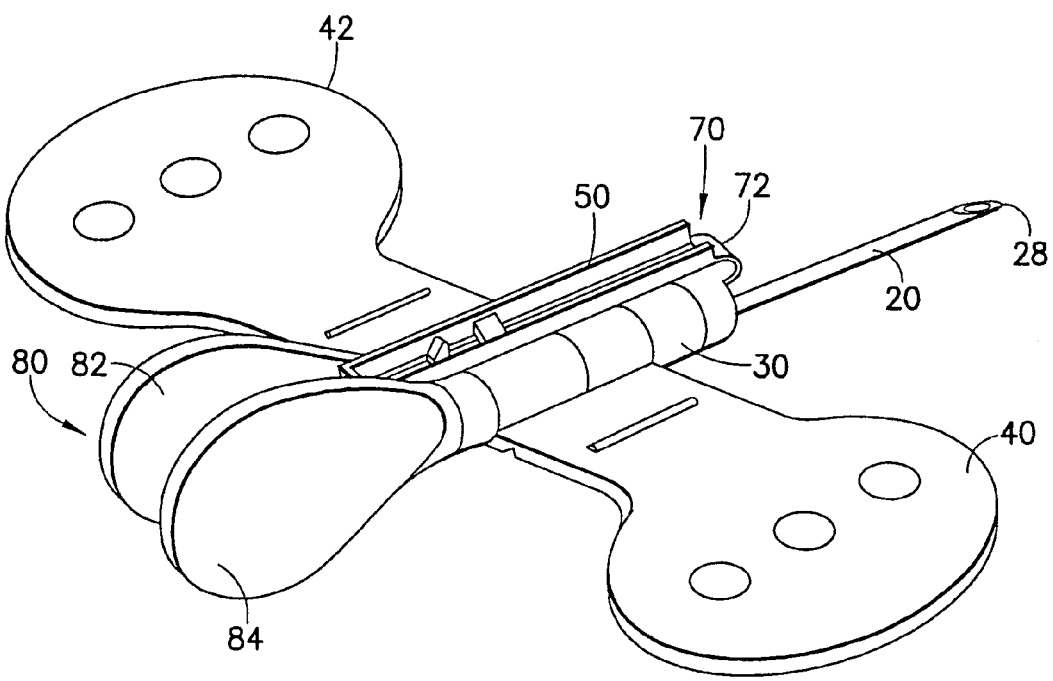
FIG. 3 is a perspective view of the needle device portion of the assembly of FIG. 1 shown with the needle shield in a retracted position.
Figure 5:
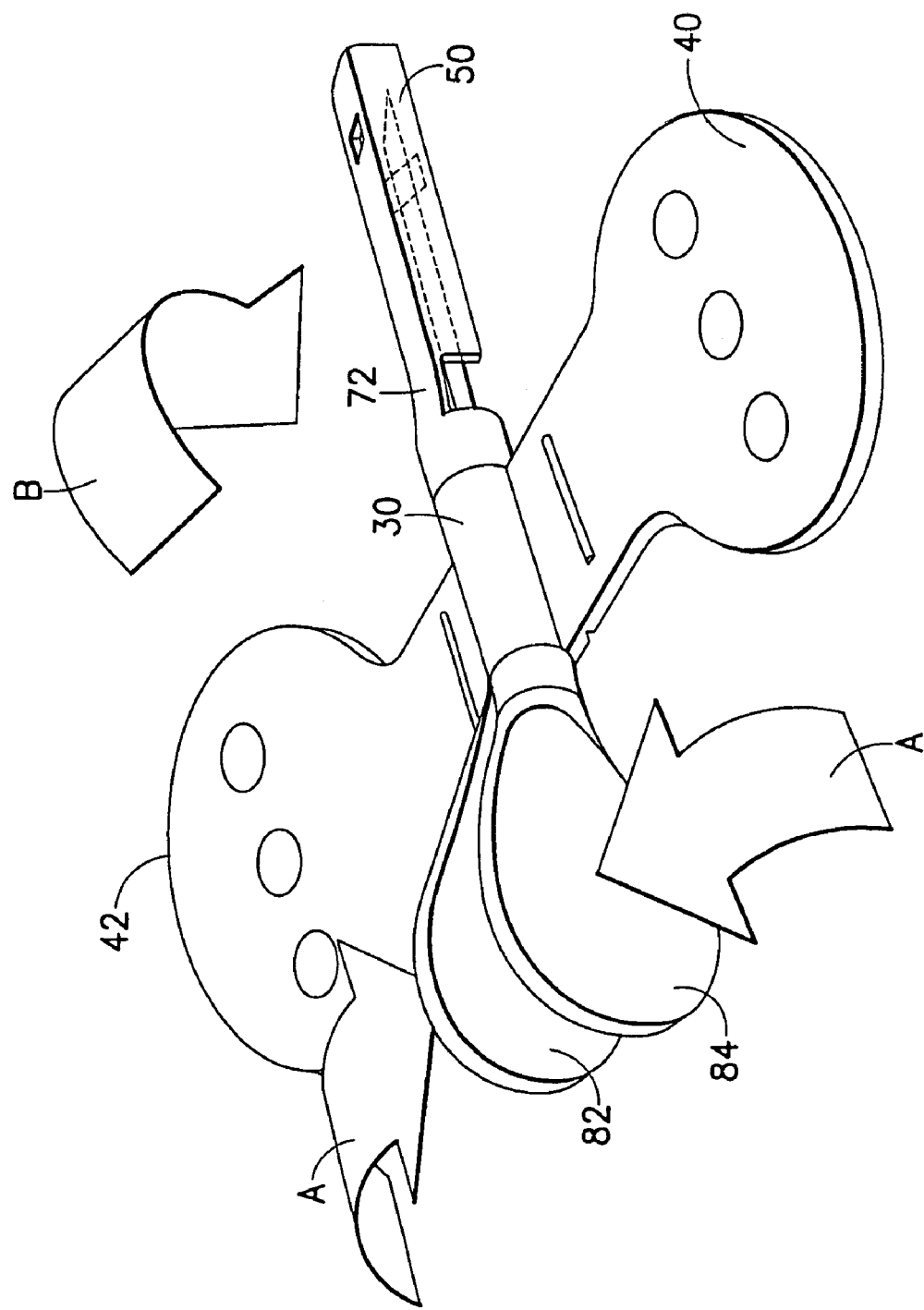
FIG. 5 is a perspective view of the needle device portion of the assembly of FIG. 1 shown with the needle shield in a fully pivoted shielding position.
Figure 6:
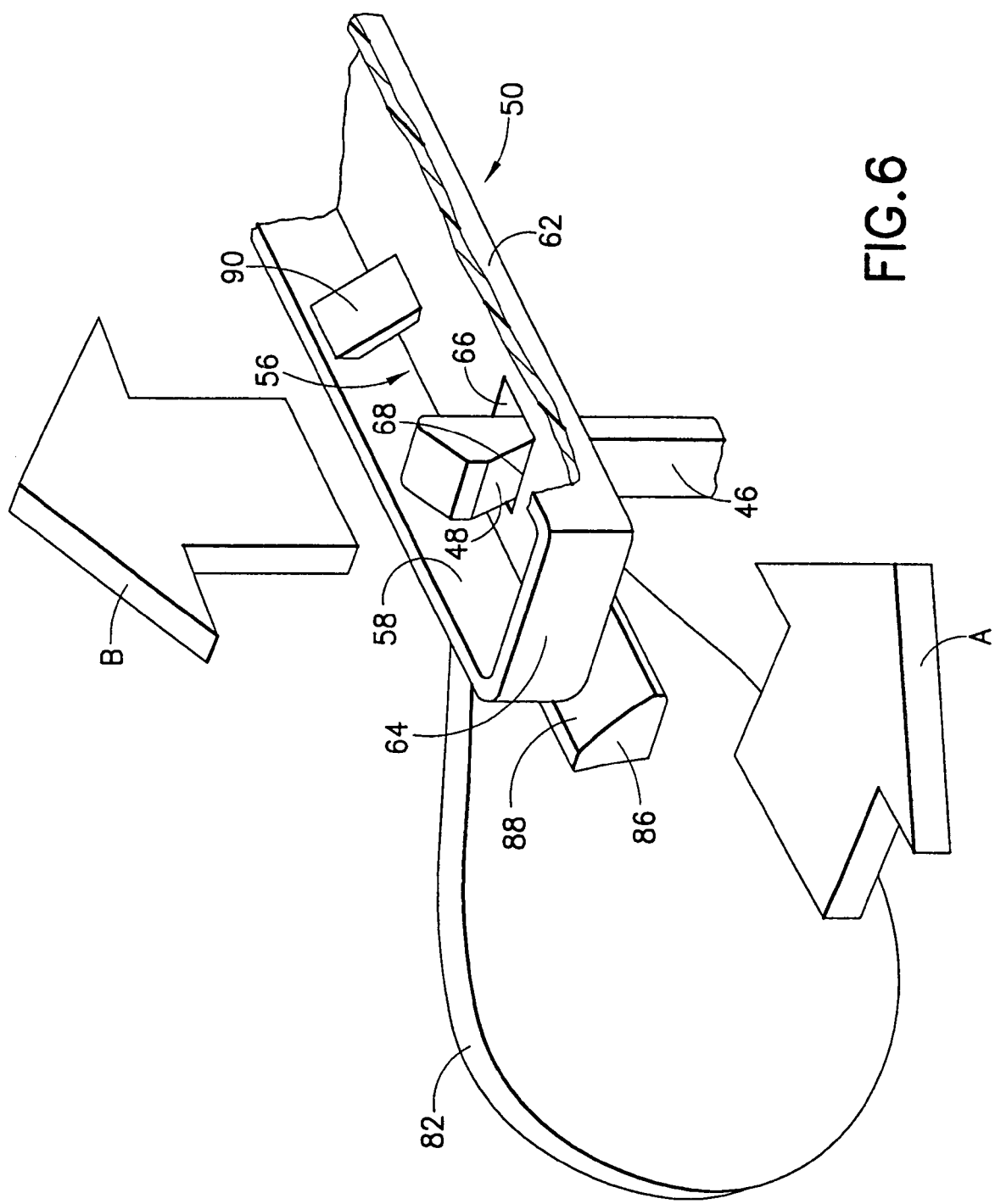
FIG. 6 is an enlarged perspective view of the release arrangement of the needle assembly of the present invention.
Figure 9:
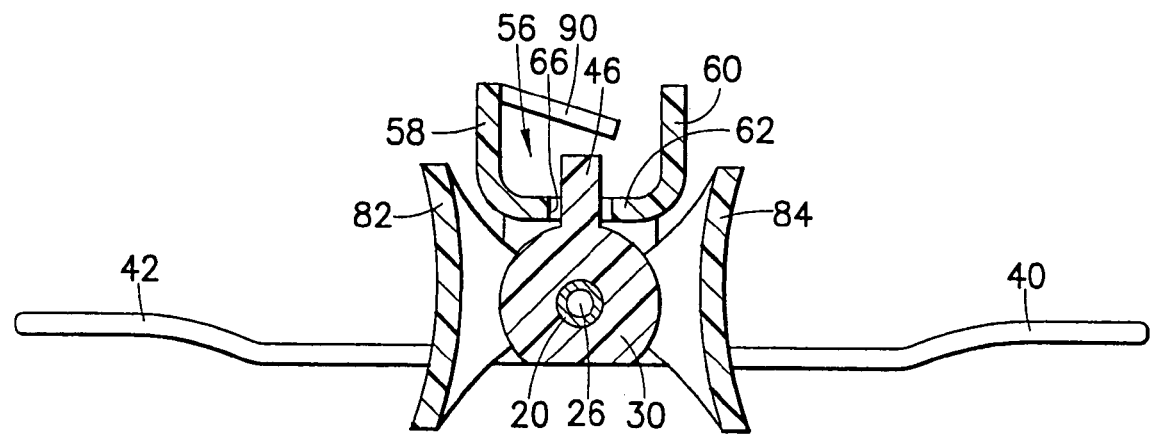
FIG. 9 is a cross-sectional view taken along line 9—9 of FIG. 7.
Figure 10:
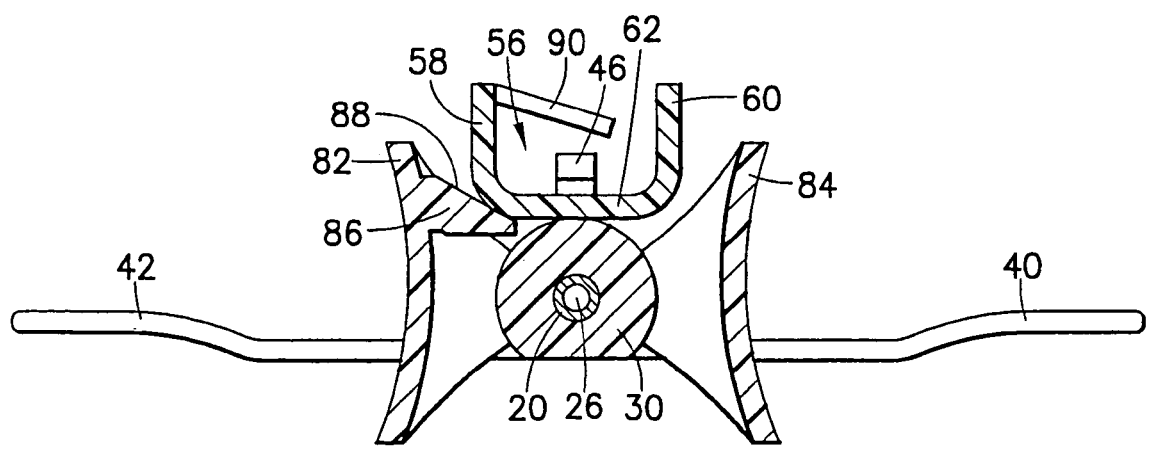
FIG. 10 is a cross-sectional view taken along line 10—10 of FIG. 7.

Shield 50 is pivotable with respect to needle cannula 30 about a pivoting hinge axis between a retracted or non-shielded position as shown in FIGS. 3 and 7 in which shield 50 is pivotally spaced from distal end 24 of needle cannula 20, and a shielded position as shown in FIGS. 5 and 8 in which the distal end 24 and puncture tip 28 of needle cannula 20 are encompassed within slot 56 of shield 50.

Needle device 12 further includes a biasing element 70 which includes stored energy for biasing shield 50 pivotally toward the shielded position encompassing needle cannula 20. Desirably, biasing element 70 extends between the distal end 24 of hub 30 and the proximal end 52 of shield 50, and provides a biasing force between hub 30 and shield 50. Biasing element 70 may be any type of structure capable of storing energy for biasing shield 50 pivotally toward the shielding position. For example, biasing element 70 may be a wound torsion spring such as a coil spring, a compression spring, a leaf spring, or the like. Desirably, hub 30 and shield 50 comprise a one-piece structure integrally formed as a unitary structure with biasing element 70 in the form of a leaf spring 72 extending therebetween and integrally formed therewith. As such, leaf spring 72 acts as a pivot point or a pivot hinge between shield 50 and hub 30, and also provides the energy to bias shield 50 toward the shielding position.

Shield 50 is maintained in the retracted position as shown in FIGS. 3 and 7 against the bias of biasing element 70 through a latch mechanism extending between shield 50 and hub 30. For example, hub 30 may include an elongated member such as a finger or snap arm 46 extending from a top surface thereof. Snap arm 46 desirably extends perpendicular to an axis defining needle device 12. Snap arm 46 may include a tab 48 at an end surface thereof, which may be a bump or a raised portion extending toward the proximal end of needle device 12, such as shown in detail in FIG. 6. Snap arm 46 is in engagement with a portion of shield 50, and desirably extends within or through a recess or opening within shield 50, such as opening 66 extending through the top section 62 of shield 50. With such an arrangement, tab 48 of snap arm 46 frictionally engages the perimetrical edge 68 extending around opening 66 through shield 50. Such frictional engagement maintains the shield 50 in a fixed state, against the bias of biasing element 70. It is contemplated that other arrangements for the latch mechanism can be incorporated within the scope of the present invention. For example, the location of the snap arm and the recess or opening can be reversed with respect to the hub and shield, such that the snap arm extends from the shield and the recess or opening extends within the hub. Other latching arrangements are also contemplated, so long as they are capable of maintaining the shield in the first position against the biasing force of the biasing element.

A release arrangement 80 is further provided for release of the latch mechanism. Release arrangement 80 desirably extends from a portion of needle device 12 such that it is easily graspable by a user during normal use of the device. For example, release arrangement 80 may include a pair of elements such as first finger tab 82 and second finger tab 84 extending in a proximal direction of needle device 12. Desirably, first finger tab 82 and second finger tab 84 extend from opposing lateral sides of hub 30 adjacent the proximal end 32 thereof in an orientation substantially planar and parallel with an axis defining needle device 12, in a wing-like fashion extending away from proximal end 32 of hub 30. At least one of first finger tab 82 and second finger tab 84 are movable with respect to hub 30, and desirably both are movable with respect to hub 30 and with respect to each other. For example, first finger tab 82 and second finger tab 84 are preferably flexible members which are deflectable and/or squeezable toward each other.

Moreover, at least one of first finger tab 82 or second finger tab 84 includes a member for causing release of the latch mechanism which maintains shield 50 in the biased state adjacent hub 30. For example, a cam member such as cam 86 may extend inwardly from an inner surface of first finger tab 82. Cam 86 is movable with first finger tab 82 with respect to hub 30. Desirably, cam 86 includes a camming surface 88 which interacts with a portion of needle device 12 to cause release of the latch mechanism maintaining shield 50 in the biased state. In the embodiment depicted in FIG. 6 including snap arm 46 extending from hub 30 in engagement with opening 66 through the top section 62 of shield 50, camming surface 88 may interact with the outer surface of top section 62 to interferingly engage with shield 50. As such, shield 50 can be effectively released from being held in the biased state by the latch mechanism (i.e., the interference engagement between tab 48 and opening 66), as will be discussed in more detail herein with respect to use of the device. Alternatively, cam 86 may be designed to engage directly with snap arm 46 to move it, for example, in a distal direction during movement of cam 86, thereby releasing tab 48 out of engagement within opening 66.

In use, blood collection set 10 may be provided with needle device 12 assembled and including flexible tube 14 extending from needle device 12 and connected to fixture 16, as shown in FIG. 1. Blood collection set 10 is packaged with the shield 50 in the first retracted position, held against the bias of biasing member 70 through the latch mechanism provided by the interference engagement between tab 48 of snap arm 46 extending from hub 30 and the edge 68 of opening 66 through shield 50. Packaging cover 18 is also preferably designed so as to assist in holding shield 50 in the first retracted position against the bias of biasing member 70, thereby relieving any stress on the latch mechanism, i.e. the interference engagement between tab 48 and edge 68, during transportation and storing of blood collection set 10. For example, as shown in FIG. 1, packaging cover 18 frictionally engages needle device 12 about hub 30 and shield 50 while shield 50 is bent backward into the biased position, thereby maintaining shield 50 against the bias.

After removing blood collection set 10 from its package, it can be assembled with other appropriate medical equipment for use. For example, a non-patient needle assembly and a needle holder may be connected to blood collection set 10 through fixture 16.

To prepare for use of blood collection set 10, the user grasps wings 40 and 42 at opposing lateral sides of hub 30 between a thumb and forefinger, and bends wings 40 and 42 dorsally toward each other, as shown in FIG. 2 (although packaging cover 18 is desirably still in place at this point). Packaging cover 18 is then grasped and urged distally to disengage from needle device 12, thereby exposing puncture tip 28 of needle cannula 20.

The overall design and profile of needle device 12 is configured such that bending of the wings 40 and 42 to the dorsal position for positioning and placement does not cause activation of the release arrangement 80. In other words, bending of wings 40 and 42 together does not cause pinching or squeezing movement of the first finger tab 82 and second finger tab 84 relative to each other, which would cause movement of cam 86 to engage the latch mechanism and thereby release the latch mechanism from interference engagement between hub 30 and shield 50. This is desirably accomplished by positioning the first and second finger tabs 82, 84 of release arrangement 80 at a location proximal to hub 30. As such, shield 50 is maintained in the first retracted position with release arrangement 80 unactivated during bending of wings 40 and 42 for positioning and placement of needle device 12.

Figure 4:
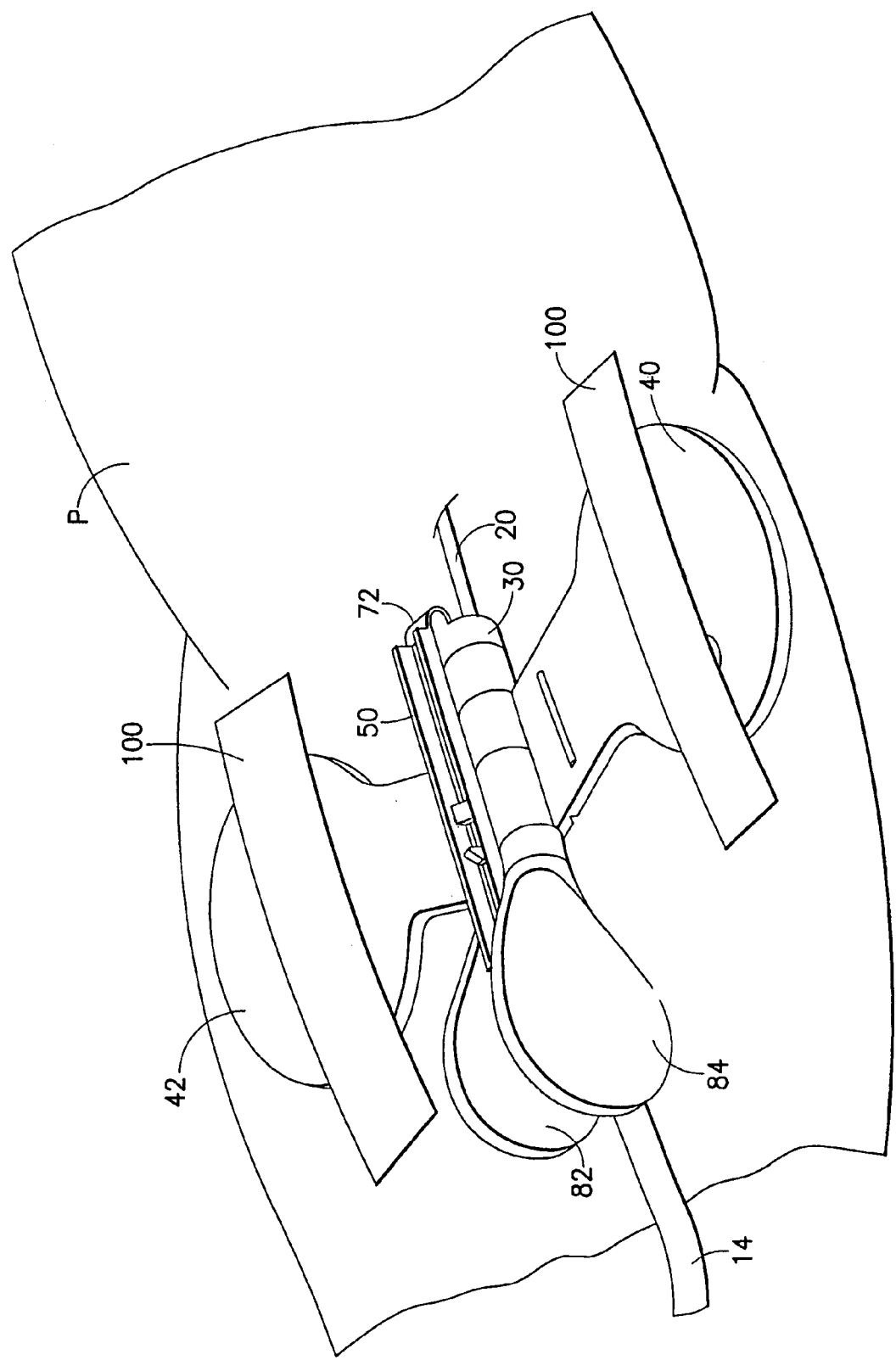
FIG. 4 is a perspective view of the needle assembly of FIG. 1 shown in use with a patient during a blood collection procedure.

After packaging cover 18 is removed, the medical practitioner can then urge puncture tip 28 at distal end 24 of needle cannula 20 into a targeted blood vessel of a patient with wings 40 and 42 bent inwardly toward each other between the user's fingers to act as a structure for guided placement, as is known in the art. After the targeted blood vessel has been accessed as shown in FIG. 4, the medical practitioner can release the grip on wings 40 and 42, and wings 40 and 42 can thereafter be taped to the skin of the patient P through tape 100, to prevent movement of the needle device 12 during use.

Figure 11:
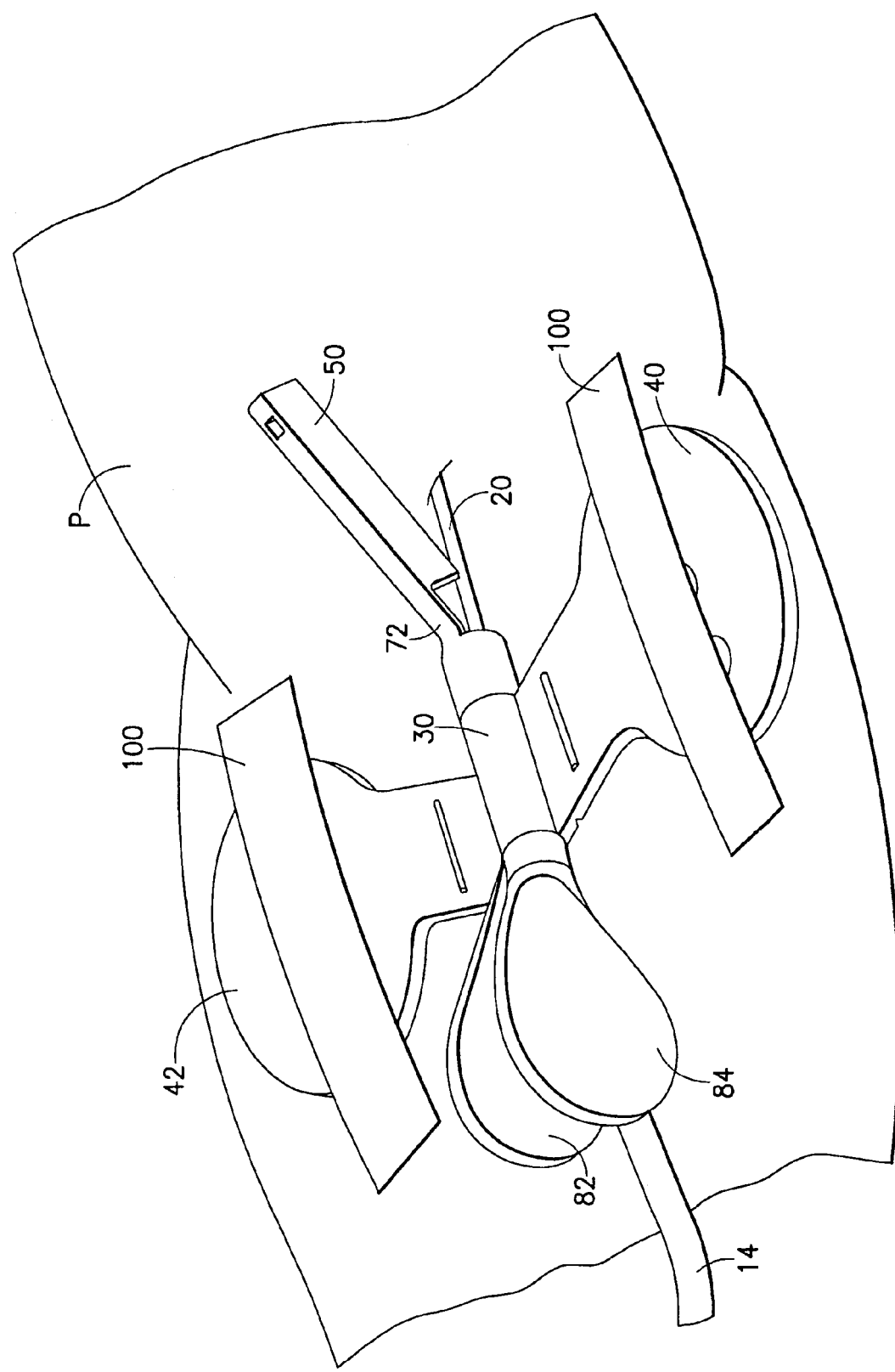
FIG. 11 is a perspective view of the needle assembly of FIG. 1 shown in use with a patient in an alternate method during a blood collection procedure.

Upon completion of the procedure, such as when all desired samples have been drawn, needle cannula 20 can be withdrawn from the patient. As opposed to conventional techniques for withdrawing wingsets by again bending the wings together in a dorsal manner, withdrawal of needle device 12 is preferably accomplished by grasping release arrangement 80, that is by grasping and/or squeezing the first finger tab 82 and second finger tab 84 between a user's thumb and forefinger while withdrawing needle device 12 from the patient. This grasping causes first finger tab 82 and second finger tab 84 to move toward each other in a direction of arrows A in FIG. 5. This movement toward each other in turn causes cam 86 to move inwardly toward hub 30, with camming surface 88 contacting and engaging the outer surface of top section 62 of shield 50. As cam 86 continues to move inwardly based on movement of first finger tab 82 and second finger tab 84 in a direction of arrows A, camming surface interferingly engages against the outer surface of top section 62, thereby forcing shield 50 in the direction of arrow B in FIG. 6. As shield 50 moves in the direction of arrow B, the force applied by the user in squeezing first and second finger tabs 82, 84 which causes movement of cam 86 overcomes the interference engagement between tab 48 and perimetrical edge 68 of opening 66. Accordingly, snap arm 46 is deflected distally, thereby releasing the interference engagement between tab 48 and edge 68. At this point, the latch mechanism established through the interference engagement between tab 48 and edge 68 is released, and shield 50 is therefore no longer held in place against the bias of leaf spring 72 by the latch mechanism. Accordingly, the energy stored in leaf spring 72 causes shield 50 to pivotally move in a direction of arrow B about a pivot axis defined by the hinge of leaf spring 72. At this point, the puncture tip 28 of needle cannula 20 may still be positioned within the patient. As such, shield 50 is propelled forward to a position in which it contacts the skin of the patient P, as shown in FIG. 11. The user can then remove the needle device 12 from the patient, during which the shield 50 continues to pivot under the bias of the leaf spring 72, until the needle cannula 20 is fully withdrawn from the patient, at which point the shield 50 extends to the fully shielding position completely encompassing puncture tip 28.

At this point, needle cannula lock 90 engages needle cannula 20. Thus, a return movement of shield 50 is prevented through needle cannula lock 90 acting as a locking mechanism. Hence, puncture tip 28 of needle cannula 20 is safely shielded. Blood collection set 10 may then be appropriately discarded.

Alternatively, if desired, activation of release arrangement 80 to release shield 50 can be accomplished immediately after needle cannula 20 is placed within the patient's blood vessel, as opposed to waiting for withdrawal of needle device 12 from the patient. In such a case, shield 50 is propelled forward to a position in which it contacts the skin of the patient P prior to sampling, and the sample can thereafter be collected.

Moreover, activation of release arrangement 80 may be delayed until after needle cannula 20 is fully removed from the patient. For example, wings 40 and 42 may be bent together in a dorsal manner to create a structure for holding needle device 12 and withdrawing needle cannula 20 from the patient. After the needle cannula 20 is withdrawn in this manner, activation of release arrangement 80 can be accomplished to release shield 50 and effectively shield the used puncture tip 28. As such, the needle device of the present invention is selectively passive.

The needle device of the present invention is particularly innovative since it involves a passive activation of the safety shielding feature through the ergonomic layout of the device. In particular, the shield housing is automatically activated to shield the needle cannula during the typical steps involved in a venipuncture procedure. For example, the device is easily insertable within a patient using a normal technique with bent wings forming a dorsal structure for guiding, positioning, and placement of the device. If desired, the shield housing can remain retracted during the blood sampling procedure, thereby preventing the shield housing from interfering with the user during the sampling procedure, and preventing the patient from being startled by activation of the shield against the patient's skin prior to the sampling procedure. Moreover, activation is easily accomplished through structure provided on the device for easily removing the needle device from the patient, i.e., by grasping the release arrangement provided through the first and second finger tabs. This grasping automatically passively activates the device during removal, thereby avoiding any secondary active step for shielding of the assembly by the user, and preventing any unnecessary exposure to the used needle cannula. The selectively passive activation affords a greater degree of safety to the user with minimal or no change in technique, as compared with conventional safety needle mechanisms.

While the medical device of the present invention is described in terms of several preferred embodiments for use in connection with bodily fluid collection systems and like devices, the present invention may take many different forms. The preferred embodiments shown in the drawings and described hereinabove in detail are to be considered as exemplary of the principles of the invention and are not intended to limit the invention to the embodiments illustrated. Various other embodiments will be apparent to and readily made by those skilled in the art without departing from the scope and spirit of the invention. The scope of the present invention will be measured by the appended claims and their equivalents.

The invention claimed is:

1. A safety needle assembly comprising:
   a hub having a proximal end and a distal end with a passageway extending therebetween;
   a needle cannula having a proximal end portion, a distal end portion and a lumen extending therebetween, the needle cannula extending from the distal end of the hub;
   an elongated shield pivotably movable between a first position exposing said needle cannula and a second position encompassing said needle cannula, said shield maintained in said first position through a latch mechanism extending between said shield and said hub;
   a biasing element biasing the shield toward the second position; and
   a release arrangement comprising a movable member extending from the hub and movable with respect to said hub, such that movement of said movable member causes engagement of said movable member with said latch mechanism, thereby causing release of said latch mechanism and causing said biasing element to bias said shield toward said second position,
   wherein said moveable member of said release arrangement comprises a first finger tab including a camming surface, said camming surface adapted for engagement with said latch mechanism upon movement of said first finger tab so as to release said latch mechanism, thereby causing said biasing element to bias said shield toward said second position.

2. A safety needle assembly as in claim 1, wherein said latch mechanism comprises an elongate member extending from said hub and in frictional engagement with a recess or opening in said shield.

3. A safety needle assembly as in claim 2, wherein said elongate member includes a tab on an end surface thereof, said tab extending within and in frictional engagement with said recess or opening in said shield.

4. A safety needle assembly as in claim 3, wherein movement of said first finger tab causes said camming surface to cam said tab out of frictional engagement with said recess or opening in said shield.

5. A safety needle assembly as in claim 1, further comprising a second finger tab in opposing relation with said first finger tab, said first finger tab movable upon application of pressure between said second finger tab and said first finger tab.

6. A safety needle assembly as in claim 1, wherein said shield further includes structure for maintaining said shield in said second position.

7. A safety needle assembly as in claim 6, wherein said structure comprises a cannula lock extending from within a passageway of said shield for engagement with said needle cannula.

8. A safety needle assembly as in claim 1, further comprising a pair of flexible wings extending from opposing lateral sides of said hub.

9. A safety needle assembly as in claim 1, wherein said hub further comprises structure for attachment to a medical device.

10. A safety needle assembly as in claim 1, wherein said biasing element comprises a leaf spring.

11. A safety needle assembly as in claim 1, wherein said hub, said biasing element and said shield are integrally formed with said biasing element extending between the distal end of said hub housing and a proximal end of said shield.

12. A safety needle assembly as in claim 1, further comprising a removable packaging cover covering said distal end of said needle cannula.

13. A safety needle assembly as in claim 1, wherein said packaging cover assists in maintaining said shield in said first position.

14. A method for passively activating a safety needle assembly comprising:
   providing a safety needle system comprising a hub including a needle cannula extending from a distal end of said hub toward a distal puncture tip and a pivotable shield adjacent said hub, said safety needle system further including a biasing element for pivotably biasing said shield toward a shielding position encompassing said distal puncture tip of said needle cannula and a latch mechanism between said hub and said shield for maintaining said shield in a biased state adjacent said hub, said latch mechanism being releasable through engagement with a release mechanism to release said shield from said biased state;
   inserting said safety needle system into a patient; and
   grasping said release mechanism, thereby causing release of said latch mechanism and releasing said shield from said biased state and causing said shield to pivot toward said shielding position
   wherein the latch mechanism comprises an elongate member extending from said hub and in frictional engagement with a recess or opening in said shield,
   wherein said elongate member includes a tab on an end surface thereof, said tab extending within and in frictional engagement with said recess or opening in said shield, and
   wherein said release mechanism comprises a finger tab including a camming surface, and wherein said grasping step causes movement of said first finger tab which causes said camming surface to cam said tab out of frictional engagement with said recess or opening in said shield.

15. The method of claim 14, wherein said release mechanism comprises a second finger tab opposing said first finger tab, and wherein said grasping step comprises grasping said first and second finger tabs, thereby causing movement of said first finger tab with respect to said second finger tab which causes said camming surface to cam said tab out of frictional engagement with said recess or opening in said shield.

* * * * *